(12) United States Patent
Burdette et al.

(10) Patent No.: US 9,507,809 B2
(45) Date of Patent: *Nov. 29, 2016

(54) SYSTEM AND METHOD FOR PROVIDING AUTOMATICALLY UPDATED PRODUCT INSERTS

(71) Applicant: BIO-RAD LABORATORIES, INC., Hercules, CA (US)

(72) Inventors: Daniel Burdette, Richardson, TX (US); Phuong Le-Thi, Mission Viejo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 14/309,862

(22) Filed: Jun. 19, 2014

(65) Prior Publication Data

US 2014/0304223 A1 Oct. 9, 2014

Related U.S. Application Data

(62) Division of application No. 13/100,136, filed on May 3, 2011, now Pat. No. 8,799,457.

(60) Provisional application No. 61/330,833, filed on May 3, 2010.

(51) Int. Cl.
*G06F 15/173* (2006.01)
*G06F 17/30* (2006.01)
*G06F 19/00* (2011.01)

(52) U.S. Cl.
CPC ....... *G06F 17/30289* (2013.01); *G06F 19/366* (2013.01)

(58) Field of Classification Search
CPC .............. G09F 11/3672; G09F 17/30289; G09F 19/322; G09F 19/363; G09F 11/3684; G09F 17/30377; G09F 17/30424; G09F 19/324; G09F 19/3443; G09F 17/30011; G09F 19/366
USPC ........................ 709/224, 201–203, 217–219; 702/81–84, 179–186
See application file for complete search history.

(56) References Cited

U.S. PATENT DOCUMENTS 6,295,506 B1 9/2001 Heinonen et al.
8,799,457 B2 8/2014 Burdette et al.
(Continued)

FOREIGN PATENT DOCUMENTS

| CN | 1711548 A | 12/2005 |
|----|-----------|---------|
| JP | 2007-507138 A | 3/2007 |
| JP | 2007-122183 A | 5/2007 |
| JP | 2007-514207 A | 5/2007 |
| JP | 2007-248088 A | 9/2007 |
| WO | 01/67113 A1 | 9/2001 |

OTHER PUBLICATIONS

First Office Action, mailed Feb. 24, 2015, in Japanese Application No. 2013-509177, 6 pages. (including English Translation).
(Continued)

*Primary Examiner* — Ruolei Zong
(74) *Attorney, Agent, or Firm* — Kilpatrick Townsend & Stockton

(57) ABSTRACT

Systems, apparatuses, and methods can provide parameters of operating results for control products used in biological reactions. For example, automatically updated inserts containing such parameters for clinical quality controls can be provided. A customer can log into a website, provide lot number of quality control products, information about instruments, and tests being performed and then receive updated parameters for the products. The product inserts can be customized for or by a particular customer.

40 Claims, 15 Drawing Sheets

(56) References Cited

U.S. PATENT DOCUMENTS

| | | | |
|---|---|---|---|
| 2003/0036683 | A1 | 2/2003 | Kehr et al. |
| 2003/0109904 | A1 | 6/2003 | Silver et al. |
| 2005/0010781 | A1 | 1/2005 | Harper et al. |
| 2005/0148084 | A1* | 7/2005 | Parce ............... B01L 3/5027 436/50 |
| 2007/0135997 | A1 | 6/2007 | Hytopoulos |
| 2007/0198213 | A1 | 8/2007 | Parvin et al. |
| 2008/0046510 | A1 | 2/2008 | Beauchamp et al. |
| 2009/0063259 | A1 | 3/2009 | Cyrus et al. |
| 2009/0222400 | A1* | 9/2009 | Kupershmidt ....... G06N 99/005 706/52 |

OTHER PUBLICATIONS

Notice of First Office Action, dated Feb. 16, 2015, in Chinese Patent Application No. 201180022377.1, 20 pages. (including English Translation).

International Search Report and Written Opinion in counterpart PCT/US11/34991, 12 pages.

"Mitteilung des Europäischen Patentamts vom 1. Oktober 2007 über Geschäftsmethoden = Notice from the European Patent Office dated Oct. 1, 2007 concerning business methods = Communiqué de l'Office européen des brevets,en date du 1er octobre 2007, concernan", Journal Officiel de l'Office Europeen des Brevets. Official Journal of the European Patent Office.Amtsblattt des Europaeischen Patentamts, vol. 30, No. 11, Nov. 1, 2007, pp. 592-593.

"Statement in accordance with the Notice from the European Patent Office dated Oct. 1, 2007 concerning business methods-Erklaerung Gemaess der Mitteilung des Europaeischen Patentamts vom 1.OKTOBER 2007 Ueber Geschaeftsmethoden—EPU I Declaration Conforme", XP002456252, Nov. 1, 2007, 1 page.

AU2011248271 , "First Examiner Report", Dec. 15, 2015, 4 pages.

CN201180022377.1 , "Office Action", Oct. 29, 2015, 17 pages.

CN201180022377.1 , "Office Action", Apr. 22, 2016, 7 pages.

EP11778166.6 , "Extended European Search Report", Feb. 17, 2014, 6 pages.

EP11778166.6 , "Office Action", Apr. 1, 2016, 9 pages.

\* cited by examiner

Liquichek™ Immunoassay Plus Control
Levels 1, 2 and 3

| REF | 360 Trilevel 12 x 5 mL<br>361 Level 1 12 x 5 mL<br>362 Level 2 12 x 5 mL<br>363 Level 3 12 x 5 mL<br>360X Trilevel Minipak 3 x 5 mL | CE 0197 | IVD | EXP YYYY-MM-DD | LOT XXXXD | Level 1 XXXX1<br>Level 2 XXXX2<br>Level 3 XXXX3 |

Revision Date 2009-08-12 → Indicates updated values

INSTRUMENT / METHOD

| | Units | Level 1 - XXXX1 Mean | Range | Level 2 - XXXX2 Mean | Range | Level 3 - XXXX3 Mean | Range |
|---|---|---|---|---|---|---|---|
| ABBOTT ARCHITECT | | | | | | | |
| Amikacin | μg/mL | XXXXX | XXXXX ~ XXXXX | XXXXX | XXXXX ~ XXXXX | XXXXX | XXXXX ~ XXXXX |
| DHEA Sulfate → | μg/dL | 97.9 | 78.4 ~ 118 | 174 | 139 ~ 209 | 729 | 583 ~ 875 |
| Ferritin | ng/mL | 22.6 | 18.1 ~ 27.1 | 215 | 172 ~ 258 | 468 | 374 ~ 562 |
| FSH | mIU/mL | 9.24 | 7.39 ~ 11.1 | 32.2 | 25.7 ~ 38.6 | 48.6 | 38.9 ~ 58.3 |
| Gentamicin | μg/mL | 3.40 | 2.72 ~ 4.08 | 5.70 | 4.56 ~ 6.83 | 7.10 | 5.68 ~ 8.52 |
| Total Beta-hCG (Intact + Beta) | mIU/mL | 4.09 | 3.27 ~ 4.91 | 20.0 | 16.0 ~ 24.0 | 365 | 292 ~ 437 |
| Immunoglobulin E | IU/mL | 39.6 | 31.6 ~ 47.5 | 67.3 | 53.9 ~ 80.8 | 286 | 228 ~ 357 |
| Insulin | μIU/mL | 41.1 | 37.9 ~ 45.1 | 74.8 | 66.1 ~ 82.9 | 150 | 137 ~ 162 |
| LH | mIU/mL | 4.16 | 3.33 ~ 4.99 | 14.8 | 11.8 ~ 17.8 | 46.6 | 37.3 ~ 55.9 |
| Phenobarbital | μg/mL | 10.6 | 8.49 ~ 12.7 | 26.1 | 20.9 ~ 31.3 | 50.0 | 46.6 ~ 60.0 |
| Phenytoin | μg/mL | 6.51 | 5.21 ~ 7.81 | 13.3 | 10.6 ~ 15.9 | 22.5 | 18.0 ~ 27.0 |
| Progesterone → | ng/mL | 0.793 | 0.634 ~ 0.952 | 8.67 | 6.94 ~ 10.4 | 18.9 | 15.1 ~ 22.7 |
| Prolactin | ng/mL | 9.45 | 7.56 ~ 11.3 | 21.3 | 17.1 ~ 25.6 | 53.5 | 42.8 ~ 64.2 |
| BECKMAN COULTER ACCESS / 2 / II | | | | | | | |
| T3 Free | pg/mL | 2.21 | 1.77 ~ 2.65 | 5.28 | 4.22 ~ 6.33 | 10.7 | 8.58 ~ 12.9 |
| T3 Total | ng/mL | 0.899 | 0.720 ~ 1.08 | 1.71 | 1.37 ~ 2.05 | 2.76 | 2.21 ~ 3.31 |
| | Uptake | | | | | | |
| T3 Uptake | Units | 1.61 | 1.29 ~ 1.93 | 0.913 | 0.730 ~ 1.10 | 0.886 | 0.709 ~ 1.06 |
| T4 Free | ng/dL | 0.852 | 0.681 ~ 1.02 | 2.38 | 1.89 ~ 2.85 | 4.73 | 3.78 ~ >6.00 |
| T4 Total → | μg/dL | 8.09 | 6.47 ~ 9.70 | 11.7 | 9.33 ~ 14.0 | 18.9 | 15.1 ~ >24.0 |
| TSH | μIU/mL | 0.728 | 0.582 ~ 0.874 | 5.31 | 4.25 ~ 6.38 | 29.2 | 29.2 ~ 30.3 |
| Vitamin B₁₂ | pg/mL | 236 | 189 ~ 283 | 444 | 355 ~ 533 | 576 | 461 ~ 691 |
| SIEMENS ADVIA CENTAUR XP | | | | | | | |
| Acetaminophen | μg/mL | 13.7 | 11.0 ~ 16.5 | 47.9 | 38.3 ~ 57.5 | 127 | 102 ~ 153 |
| AFP | ng/mL | 26.3 | 21.1 ~ 31.6 | 125 | 99.8 ~ 150 | 277 | 221 ~ 332 |
| Carbamazepine | μg/mL | 2.85 | 2.28 ~ 3.42 | 9.09 | 7.27 ~ 10.9 | 14.1 | 11.3 ~ 16.9 |
| CEA | ng/mL | 3.32 | 2.65 ~ 3.98 | 21.8 | 17.4 ~ 26.1 | 46.0 | 36.8 ~ 55.2 |
| CK-MB (Isoenzyme) | ng/mL | 3.52 | 2.81 ~ 4.22 | 16.8 | 13.4 ~ 20.1 | 36.4 | 29.1 ~ 43.6 |
| Cortisol → | μg/dL | 4.17 | 2.42 ~ 5.92 | 22.5 | 18.0 ~ 26.9 | 36.7 | 29.4 ~ 44.1 |
| Digoxin | ng/mL | 0.738 | 0.590 ~ 0.885 | 1.93 | 1.54 ~ 2.32 | 3.05 | 2.44 ~ 3.66 |
| Estradiol | pg/mL | 52.0 | 41.6 ~ 62.4 | 163 | 130 ~ 195 | 601 | 481 ~ 721 |
| PSA | ng/mL | 0.238 | 0.190 ~ 0.286 | 2.11 | 1.68 ~ 2.53 | 19.6 | 15.6 ~ 23.4 |

FIG. 1B

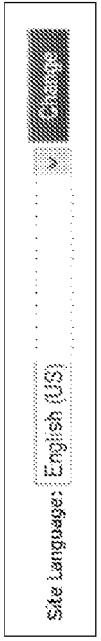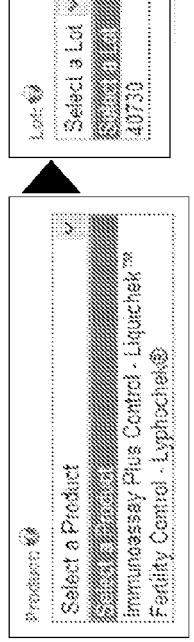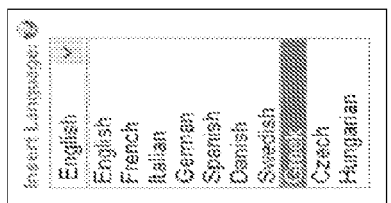
Set the Website Language
This will be defaulted to the language of your web browser.
Select:
1. Product
2. Lot
3. Insert Language
Click the Get Data Chart Info Button
FIG. 4A

4 Select Chart Units
Choose from: Conventional, SI or Choose for Each Assay

5 Check Instructions for Use (IFU) – Optional
This choice allows you to create an IFU in other languages.

8 Save Selection to My eInserts
Once complete with your selections, click this button

9 Create New Custom Insert
To start over, click Change Product, Lot or Language

My eInserts™
Update Notification

Click the lot number for the updated product insert

[Updated Instrument/Method Section]

| Lot # | Instrument/Method | Analyte(s) |
|---|---|---|
| 40230 | Abbott Architect | DHEA Sulfate, T3 Free, Progesterone, T4 Free |
| | Siemens Advia Centaur XP | Cortisol |
| | Syva Emit 2000, Genzyme Diagnostics | Acetaminophen |

[Updated Instrument/Method Section]

| Lot # | Instrument/Method | Analyte(s) |
|---|---|---|
| 19293 | Roche / Hitachi Cobas C Systems, Roche Hitachi / Modular | Cholesterol LDL |

Go to QCNet™
Log on to QCNet™ to view My eInserts or change your settings.

This is an automated message, please do not reply. To discontinue these update notifications, log on to QCNet and unsubscribe under My Account settings. Contact Us

FIG. 5

Liquichek™ Immunoassay Plus Control
Levels 1, 2 and 3

REF
[list items]

IVD   EXP YYYY-MM-DD   LOT XXXXX

Level 1   xxxxx1
Level 2   xxxxx2
Level 3   xxxxx3

Revision Date 2009-08-12 — Rev Date

→ Indicates updated values

| | Units | Level 1 - XXXX1 | | Level 2 - XXXX2 | | Level 3 - XXXX3 | |
|---|---|---|---|---|---|---|---|
| | | Mean | Range | Mean | Range | Mean | Range |
| INSTRUMENT / METHOD | | | | | | | |
| ABBOTT ARCHITECT | | xxxxx | xxxxx - xxxxx | xxxxx | xxxxx - xxxxx | xxxxx | xxxxx - xxxxx |
| [analyte] | pg/mL | 97.9 | 78.4 - 118 | 174 | 139 - 209 | 729 | 583 - 875 |
| DHEA Sulfate → | | | | | | | xxxxx |

FIG. 7

SYSTEM AND METHOD FOR PROVIDING AUTOMATICALLY UPDATED PRODUCT INSERTS

CROSS-REFERENCES TO RELATED APPLICATIONS

The present application is a divisional of U.S. patent application Ser. No. 13/100,136, entitled "System and Method for Providing Automatically Updated Product Inserts" by Burdette et al., filed on May 3, 2011, which claims priority from and is a non-provisional application of U.S. Provisional Patent Application No. 61/330,833, entitled "System and Method for Providing Automatically Updated Product Inserts" by Burdette et al., filed on May 3, 2010, both of which are herein incorporated by reference in their entireties for all purposes.

BACKGROUND

Embodiments of the present invention are generally directed to quality control products for biological and/or chemical processes, and more specifically to updates for the quality control products (e.g., insert information that accompanies a control reagent).

In biological research and manufacturing, reagents are combined with a sample in a reaction, e.g., to test a vitamin level of a blood sample. The reaction may create a result, such as a final product or just a measurement of the reaction. A control is often included in the reaction to confirm a quality of the reaction, e.g., an accuracy or efficacy. For example, the control can confirm that a test of vitamin D in a sample is accurate by analyzing output results for the control. Often, the output is expressed as a range of acceptable values for a measurement related to the control. The control can be sold for use in many different types of reactions.

Clinical quality control (QC) products typically have product inserts that contain instructions for use and contain warnings. For certain controls, e.g., assayed controls, charts of assay targets and ranges of parameters for a variety of test methods and instruments can also be provided. An example of the parameters can be an average value and a maximum and minimum value within a standard deviation, which can be compared to results of a test. For manufactures that serve a global market, many different languages are required and various aspects of the product inserts need to be updated on occasion.

Current methods are costly in providing the updates, and the updates are provided infrequently. Therefore it is desirable to provide more efficient ways of providing inserts and updates for inserts.

BRIEF SUMMARY

Embodiments can provide systems, apparatuses, and methods for providing parameters of operating results for control products used in biological reactions. In one aspect, automatically updated inserts containing such parameters for clinical quality controls can be provided. In another aspect, the product inserts can be customized for or by a particular customer. For example, the parameters for an insert can be generated on demand by a network server, e.g., a web server on the Internet.

Various embodiments can provide: easy access to the most current quality control (QC) values online; customization of the product insert to fit a particular customer's needs (e.g. a customer can select the instruments, methods, units and language desired); automatic notification when there are updates for a particular insert (e.g. updated parameters for any of the tests for an insert), which can be provided by email when a change has been made to the customer's insert; larger font size for easier readability; and additional languages to support international customers.

According to one embodiment, a method of providing parameters of operating results for control products used in biological reactions. A server system receives, from a user, a request for parameters relating to one or more tests using the control product. The server system identifies the parameters corresponding to the request. The parameters are sent to the user.

According to another embodiment, a method of obtaining parameters of operating results for control products used in biological reactions is provided. A customer receives a control product. The customer sends a request to a server system for parameters relating to one or more tests using the control product, wherein the server system identifying the parameters corresponding to the request. The customer receives the parameters from the server system.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 1B illustrates data charts containing parameters of operating results of tests that use the control product according to embodiments of the present invention.

FIG. 4A-4D show a method of customizing an electronic insert according to embodiments of the present invention.

FIG. 5 shows an example of an e-mail notification that parameters have been updated for certain entries according to embodiments of the present invention.

FIG. 7 shows an electronic insert with updates marked according to embodiments of the present invention.

DETAILED DESCRIPTION

In biological research and manufacturing, a control is often included in the reaction to confirm a quality of the reaction, e.g., an accuracy or efficacy. Often, the output is expressed as a range of acceptable values for a measurement related to the control. The control can be sold for use in many different types of reactions. Clinical quality control (QC) products typically have product inserts that contain instructions for use and contain warnings. For certain controls, e.g., assayed controls, charts of assay targets and ranges of parameters for a variety of test methods and instruments can also be provided. An example of the parameters can be an average value and a maximum and minimum value within a standard deviation, which can be compared to results of a test. For manufactures that serve a global market, many different languages are required and various aspects of the product inserts need to be updated on occasion.

In various aspects, inserts for QC products can automatically be updated, and electronically sent to a customer upon request. The product inserts can be customized for or by a particular customer. For example, the parameters for an insert can be generated on demand by a network server, e.g., a web server on the Internet.

I. Overview

Figure 1A:
FIG. 1A illustrates instructions for performing one or more tests using a control product according to embodiments of the present invention.

FIG. 1A illustrates instructions for performing one or more tests using a control product according to embodiments. In various embodiments, the instructions can provide information regarding the intended use of the control product, the storage of the product, stability of the product, and other information. For the intended use, the instructions can provide information for obtaining assayed values. FDA stability claims as to quality of a product can also be provided.

FIG. 1B illustrates data charts containing parameters of operating results of tests (also called targets) that use the control product according to embodiments. The values in the data charts can provide expected values for instruments and test methods. In one embodiment, each test has parameters that include a mean and low and high ranges (e.g. based on standard deviation from a statistical sampling).

The instructions and the data chart, or each individually, can be part of an insert that is shipped with the control product. Product inserts are normally printed and packaged with the control products, and are included in every box of controls. The production of control product inserts is regulated by the FDA and falls under good manufacturing practices. In one aspect, control product inserts are to be produced according to a well defined set of FDA approved procedures that dictate how insert values are acquired, computed, checked, approved, and published.

In general, a given customer will use only a subset of the information contained in an insert. Most control product inserts contain more analytes and test methods than are used in any single laboratory. For example, an insert might contain assays for 20 different instruments while a particular laboratory may have only one of the instruments. Thus, out of the 45 analytes listed, the single laboratory might only be testing 25 of them. The extraneous analytes and test methods can be a distraction and increase the risk of a customer using the wrong values.

Printed product inserts contain the best estimates for the parameters available at the time of manufacture for appropriate control product targets and ranges. Additional product performance data can be collected from the field as customers use the product, resulting in updated targets and ranges more appropriate for current circumstances. As one example, an updated range can arise from new results due to new reagents being used with the control, which can cause a shift in the acceptable ranges of the parameters. As another example, updated ranges can also result from new data being received regarding reactions that are known to be accurate. Unfortunately, producing revised printed inserts is costly and there are no efficient mechanisms for delivering updates of inserts to customers.

In some embodiments, product inserts and/or updates of the inserts can be provided electronically. In one implementation, the data charts can be tailored to the specific tests that the specific user is performing, thus removing extraneous analytes and test methods. Also, the cost and time of preparation can be reduced, as only specified languages can be provided. Timely updates can also be provided, e.g., by monitoring when parameters change and sending notifications.

In one aspect, the instructions can change less often than the parameters in the data charts can change. Thus, in one embodiment, just the data charts can be provided as electronic inserts. Accordingly, in one embodiment, instructions can still be printed on paper. An initial data chart can also be provided at a time of mailing the product, if so desired.

Figure 2:
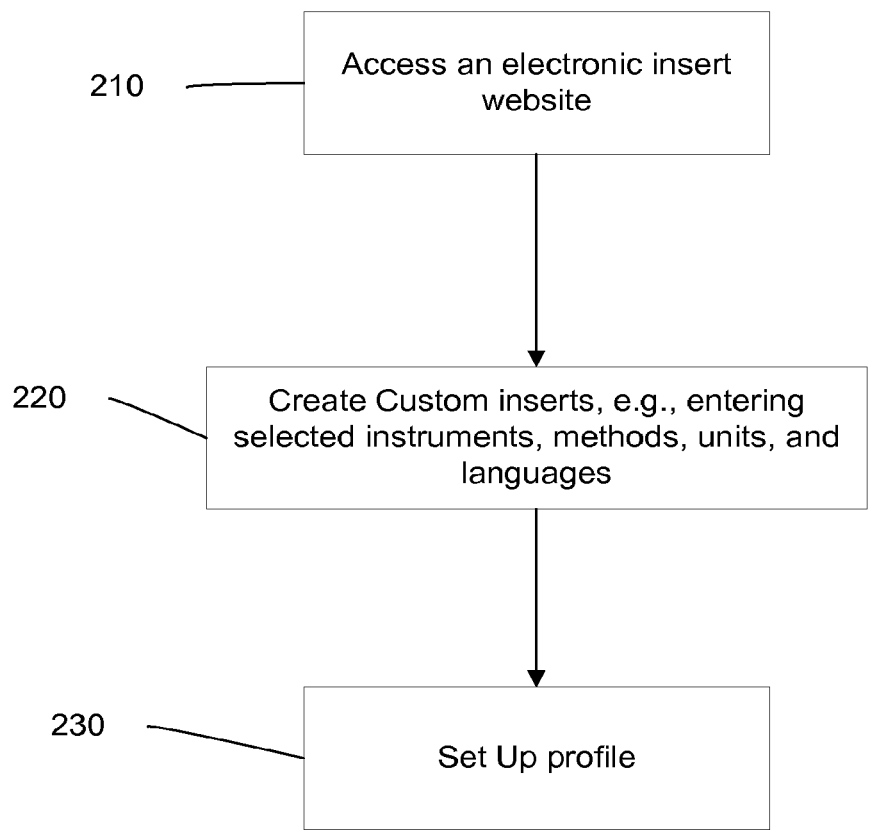
FIG. 2 is a flow chart illustrating a method for providing electronic inserts according to embodiments of the present invention.

FIG. 2 is a flow chart illustrating a method 200 for providing electronic inserts according to embodiments. Method 200 describes steps taken by a customer to obtain an electronic insert from a server. Corresponding steps can be performed by the server to provide the electronic inserts.

Method 200 and any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps. Although presented as numbered steps, steps of methods herein may be performed at a same time or in a different order. Additionally, portions of these steps may be used with portions of other steps from other methods. Also, all or portions of a step may be optional. Any of the steps of any of the methods can be performed with modules, circuits, or other means for performing these steps.

In step 210, the customer accesses an electronic insert website. As examples, the customer can be an organization (e.g. a hospital) or a specific user of an organization. The website information could be sent with a regular hard copy insert, thereby providing information on how to access the website. In one embodiment, a customer can be pre-assigned a username and/or password, which can be changed in one implementation. In another embodiment, users can register freely without requiring an invitation or pre-assigned username and/or password.

In step 2, the customer can customize the insert. In various embodiments, a user can select one or more of certain instruments (e.g., from a list), methods being used (e.g., protocols or reagents being used), units, and languages. The website can received the customized information and use it to determined one or more characteristics for an insert or an update to an insert.

In step 3, the customer can set up a profile and save the customized insert as an entry (e.g. in a storage area, called My eInserts herein). In one embodiment, the profile can have different entries for different customizations of a same product or different entries for different products. For example, a hospital might use a product in different ways, e.g., different machines, which could be in different labs of the hospital, different methods, different reagents, etc. In one implementation, a customer can view and/or modify profile information, view or edit saved custom inserts, and register for automatic notification (e.g. via e-mail).

Figure 3:
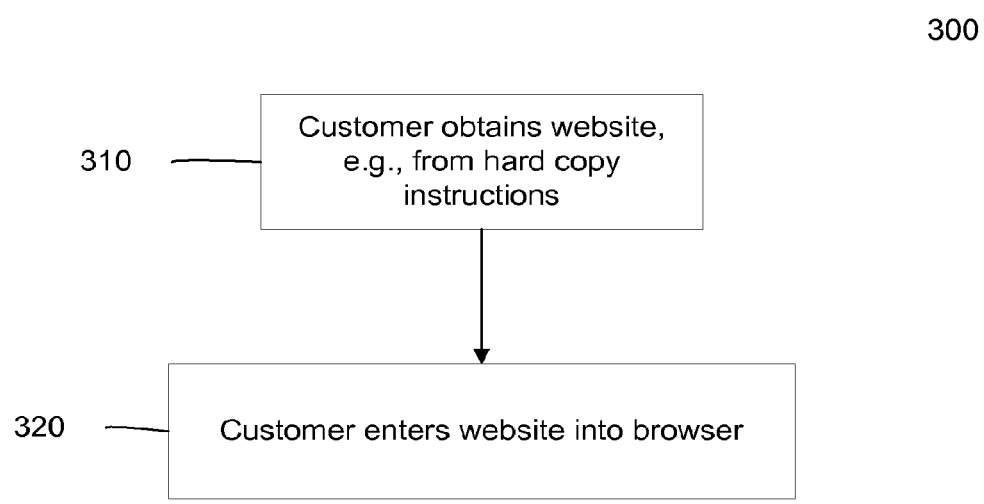
FIG. 3 shows methods of accessing the electronic insert website according to embodiments of the present invention.
Figure 4B:
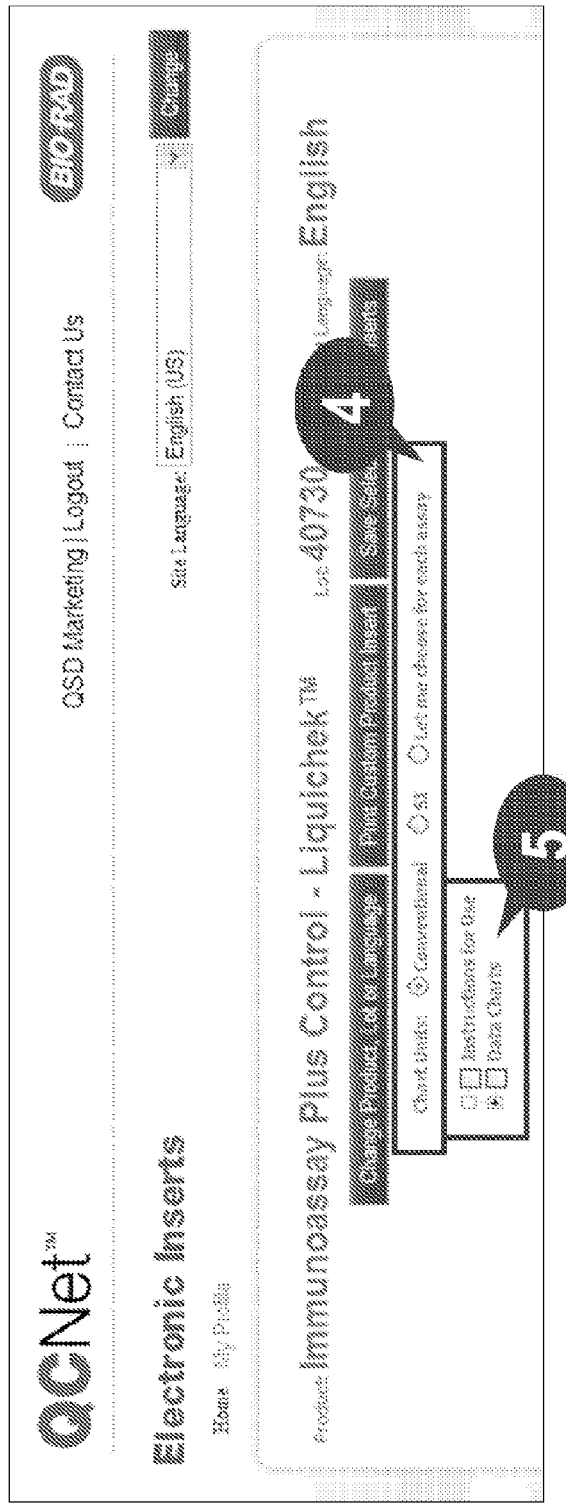
Figure 4C:
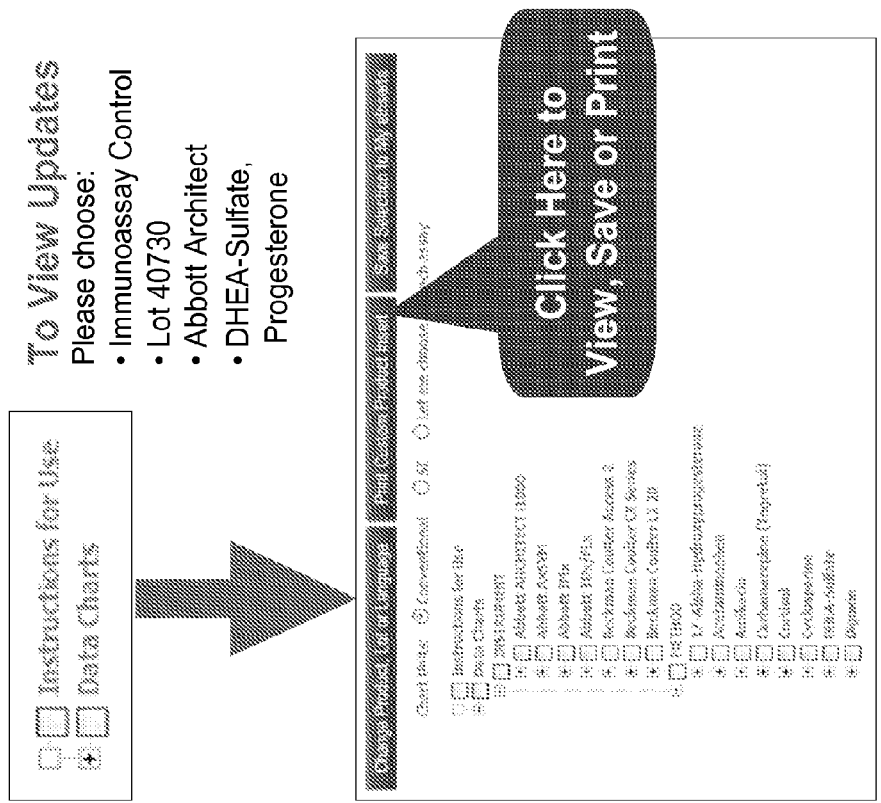
Figure 4D:
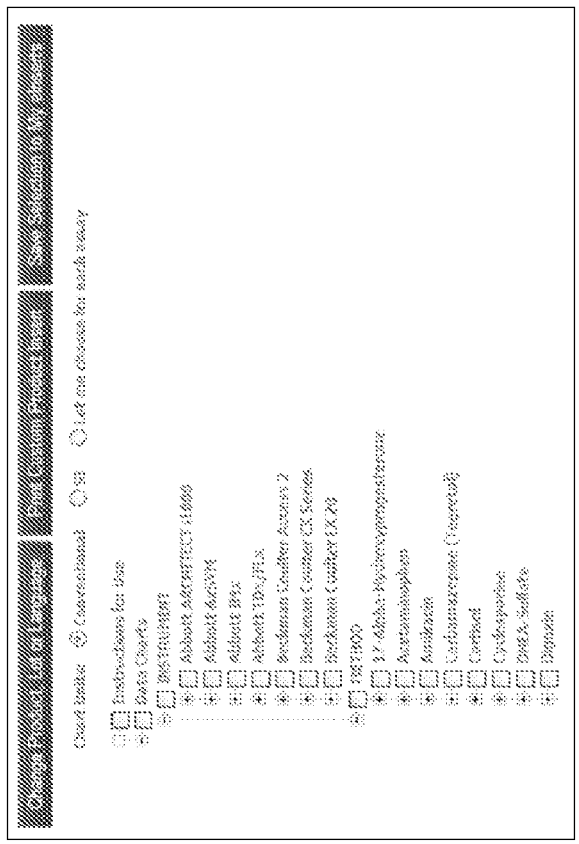

FIG. 3 is a flowchart illustrating a method 300 of accessing the electronic insert website according to embodiments. In step 310, the customer can get a server address (such as a URL), e.g., from instructions mailed with the product. In some embodiments, the instructions are packaged in each control product box. For example, the instructions can be under the heading "Instructions for Obtaining the Assignment of Values Data Sheet." In one embodiment, the instructions can read as follows. "The assignment of values data sheet is available via the internet at a domain of qcnet.com/lot#. Using the drop-down menu select the language instrument or kits and unit of measure. To receive automatic insert updates click one the 'update notification' link. To receive paper copies of the assignment of values data sheets contact a sales office."

In step 320, a customer can use the server address (e.g. a website address) into an application (e.g., a web browser) to communicate with the server, e.g., for requesting an electronic insert. In one embodiment, the website is for a specific lot number (e.g. specified by data after a backslash), which can correspond to a particular product. For example, a website could be qcnet.com/40730, which can provide direct access to a specific lot number. In various implementations, the website domain can be for all products or different web sites can be provided for different products.

In another embodiment, a general website can be used. A customer can be generally familiar with such general website, e.g., through a sales experience when buying the QC product. In one implementation, a customer can browse to a section for creating inserts (e.g. labeled "Product Inserts"). A customer can log in onto the site, where a saved profile can be accessed. Thus, when a customer creates an insert, he/she can log in to access previous data about inserts, e.g., by entering a login ID and a password. In another implementation, the customer can use a guest feature (have a guest account) to create an insert, and not log in.

FIG. 4A-4D show a method 400 of customizing an electronic insert according to embodiments. In one embodiment, various steps can be performed in different orders than presented. In another embodiment, some steps do have a certain logical progression (e.g. a step depending on one or more previous steps). In yet another embodiment, some steps may be optional. The steps of method 400 may be performed on a website of a server that can be used to request an electronic insert.

In step 1, a language can be selected for a server (e.g. a website). As shown, a user can pick a language from a list. In another embodiment, a user can type in the language. In other embodiments, the language can use defaults from the application (e.g. a web browser).

In step 2, a user interface can presented to a customer for selecting the product for which an insert is being created. The user interface can be a menu (e.g. a series of drop down menus), a list, or any other suitable mechanism for a user to enter (e.g. select) information usable to identify the product. As shown, a user can select the product and lot number (e.g. a product can be made in groups called lots). If the website was accessed with a specific address (e.g. a URL including the lot number), then the product and lot can be pre-filled when the user reaches this step. In one embodiment, different lots can have different data charts (i.e. different parameters). Also, as different products can be used for different tests, different parameters can result for the different products. In one implementation, the language for the data chart can be selected. In one embodiment, the total languages that can be selected are 27 or more.

In step 3, information for the insert (such as chart data) can be obtained, e.g., by clicking a button. In one embodiment, selection of the task of obtaining chart data can cause the website server to collect information about the product, e.g., the instruments that use the product, the tests in which the product can be used, and the units of measurement available for selection for each test. In one embodiment, the information can be stored in a database with cross-references to product and lot.

In step 4, the customer can select the units to be used for the insert. For example, various parameters of a chart can have units. In various embodiments, the units can be in conventional, SI, or other units. In one embodiment, a user can specify different units for each assay.

In step 5, the user can select if the instructions are desired, the data charts, or both. In one aspect, this step can be done at any time in the method.

In step 6, a tree can be provided for the customer to select which tests (which can be labeled methods) are going to be performed and/or which instruments are going to be used. The customer can select which ones they are using. These selections can be used to determine what parameters are put into the data chart. In one embodiment, the user is only shown parameters that are relevant to them. For example, the lot number can be used to determine which instruments and tests are relevant. In another embodiment, information from the user's profile can be used.

In some embodiments, the person can select a whole group of tests or all of the instruments for a particular type of instrument. In one embodiment, these selection can be made from a tree structure off of data charts. As shown, the customer can make selections by checking Instrument and/or Method. Activating a + sign can provide greater detail in customization. For example, the + signs can expand to allow selection of individual tests if only certain tests are desired. In one embodiment, the + sign for an instrument can cause an expanded list that shows tests that can be performed for a particular instrument. A test can appear in various places, e.g., under an instrument, or under a group of test methods.

In step 7, the customer can select view and/or print insert. In one embodiment, the request can be sent to a database that is part of the server system, which may be a system with a computer apparatus that acts as one part of the server and that is coupled with the database. The server can assemble the desired data chart from the data in the database. In one embodiment, the product, lot number, language, and list of tests and/or instruments is provided to the database to retrieve the desired parameters.

In step 8, the customer can save the selections as an entry of a profile. In one embodiment, the customer (e.g., a whole organization or a single person) can have a profile with multiple associated entries (e.g. My eInsert is an object that can show the saved entries). In this way, the server can track which product and lot number that a customer is using, and track the tests that a customer is performing with certain products and lot numbers. When the parameters for a test are updated, the customers who have a saved insert with the test selected can be notified.

In some embodiments, different people within an organization can have different logins and thus be treated as different customers, in at least this aspect. In one implementation, the customer can create multiple entries (My eInserts). For example, different entries could be for different people or different labs of an organization, where the organization can be associated with the account. The entries could be identical or have selections that are different, e.g., product, lot number, and tests. Each entry can specify a different method of notification (e.g. different phone numbers, e-mail address, IM account, etc.). Each entry can have a different name to keep track of the different entries.

In step 9, the customer insert is created. For example, a PDF (or other format) can be provided. In one embodiment, the data chart can be organized to provide the parameters next to each test or instrument selected.

FIG. 5 shows an example of an notification (e.g., an e-mail notification) that parameters have been updated for certain entries according to embodiments. In one aspect, notifications can keep a user informed of updated values for selected products, selected test methods, and/or selected instruments. As mentioned above, a user can receive a notification (e.g. e-mail, text message, phone call, etc) that a test, product, or lot number that they have selected in an entry has updated parameters. This example shows an e-mail notification, which specifies different entries for two products. In various embodiments, the notification can show the lot number, instrument/method used, and the specific controls (analytes) from the product that are used. As a product can contain multiple analytes and be used with different instruments or tests, this information can help customers to decide if a new data chart is needed.

In one embodiment, the e-mail can contain the data chart already generated. In another embodiment, the e-mail is just a notification, and can name the particular entries. The customer can then go to the web site to retrieve the new data chart, as needed. In retrieving the parameters, the customer can click on the entry, and then click a button (e.g., view and print) to create insert (e.g. a data chart).

In another embodiment, if a product or lot has numbers changed, a contact person for each entry can be contacted. In one implementation, multiple contact persons for an entry can also be specified. In one aspect, if multiple entries are affected for a same customer (login name) and the contact person is the same, then only one notification may be sent (e.g., with the e-mail specifying which entries have changed). If more than one contact person is affected, then each contact person can be notified with the specific entries associated with that contact person being identified.

In yet another embodiment, if an aspect of an instrument changes, the customer can receive a notification. For example, a customer might select a particular instrument (e.g. in step 6 of method 400), which encompasses all of the tests for the instrument even though the customer is only using some of the tests. If the parameters for a test for that instrument change, the customer can be notified regardless of which tests the customer is actually using for that instrument. In other words, the detail of notification can depend on the level of detail provided by the customer.

Figure 6:
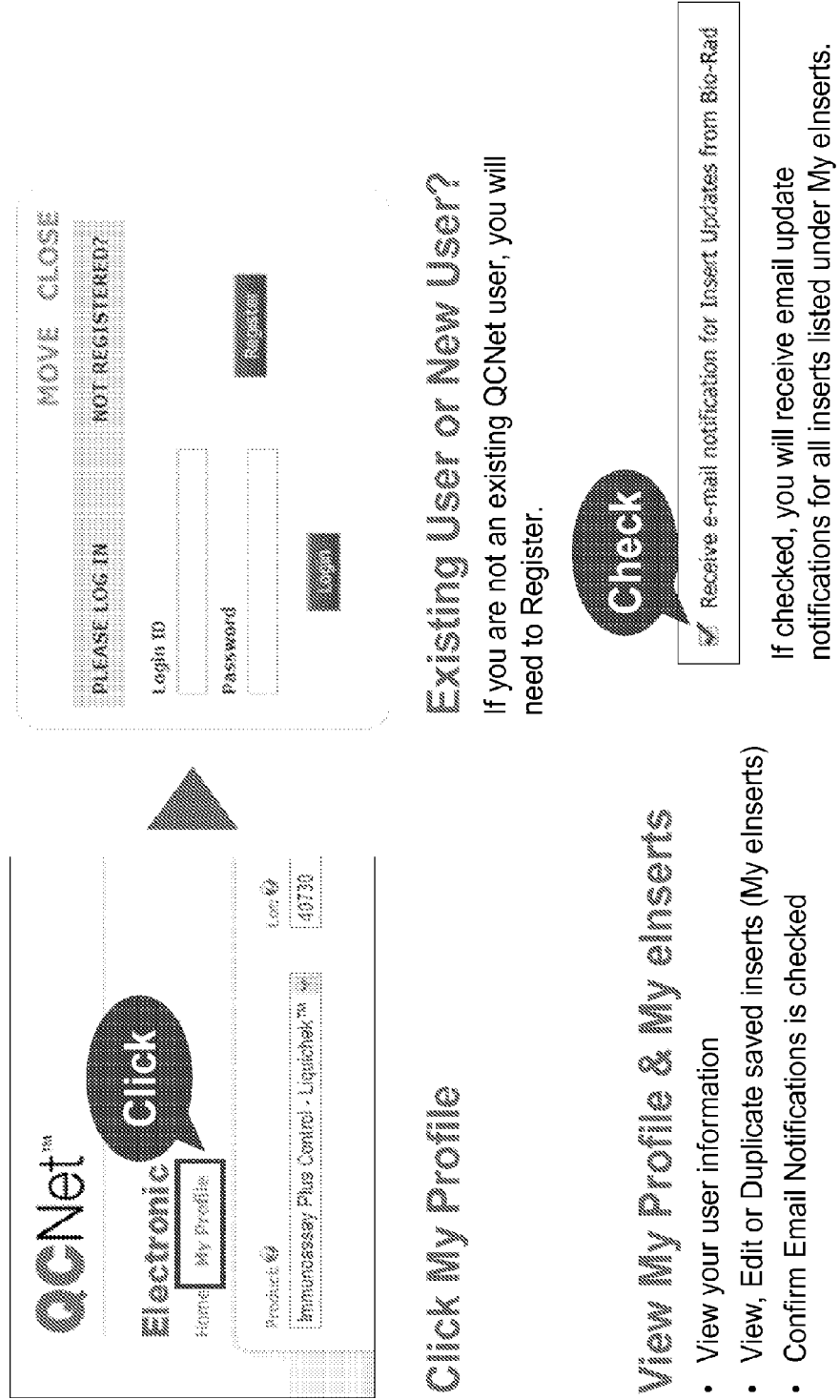
FIG. 6 shows how to modify a profile or setup a new profile according to embodiments of the present invention.

FIG. 6 shows a diagram illustrating how to modify a profile or setup a new profile according to embodiments. In one aspect, a customer can always go back into the website to regenerate an insert, e.g., via a saved profile. If the parameters have changed then a new insert would be generated.

In one embodiment, the customer can also duplicate a saved entry (My eInsert) to create a new entry with some information that is different, but the rest the same. For example, if a customer uses up a product and buys the same product again, the customer can specify the new lot number and port over (copy) the same selections previously made for the old purchase. In one implementation, the server can check to make sure that instruments and tests match, just in case those have changed from lot numbers. Also, if new test have been added, the customer could be prompted if he wants to select any of the new ones. And, if some of the test have been removed, then a warning message can be provided.

FIG. 7 shows an electronic insert with updates marked according to embodiments. Since an update is generated on demand, the latest data can be made available. Updates can be fully integrated into the data charts. In various embodiment, the new parameters can be in bold, a symbol next to the data can indicate what has changed, arrows can point to the changed data, or other mechanisms can be used. A revision date can also be supplied, e.g., so that a user can determine if the data chart has been updated recently.

Figure 8:
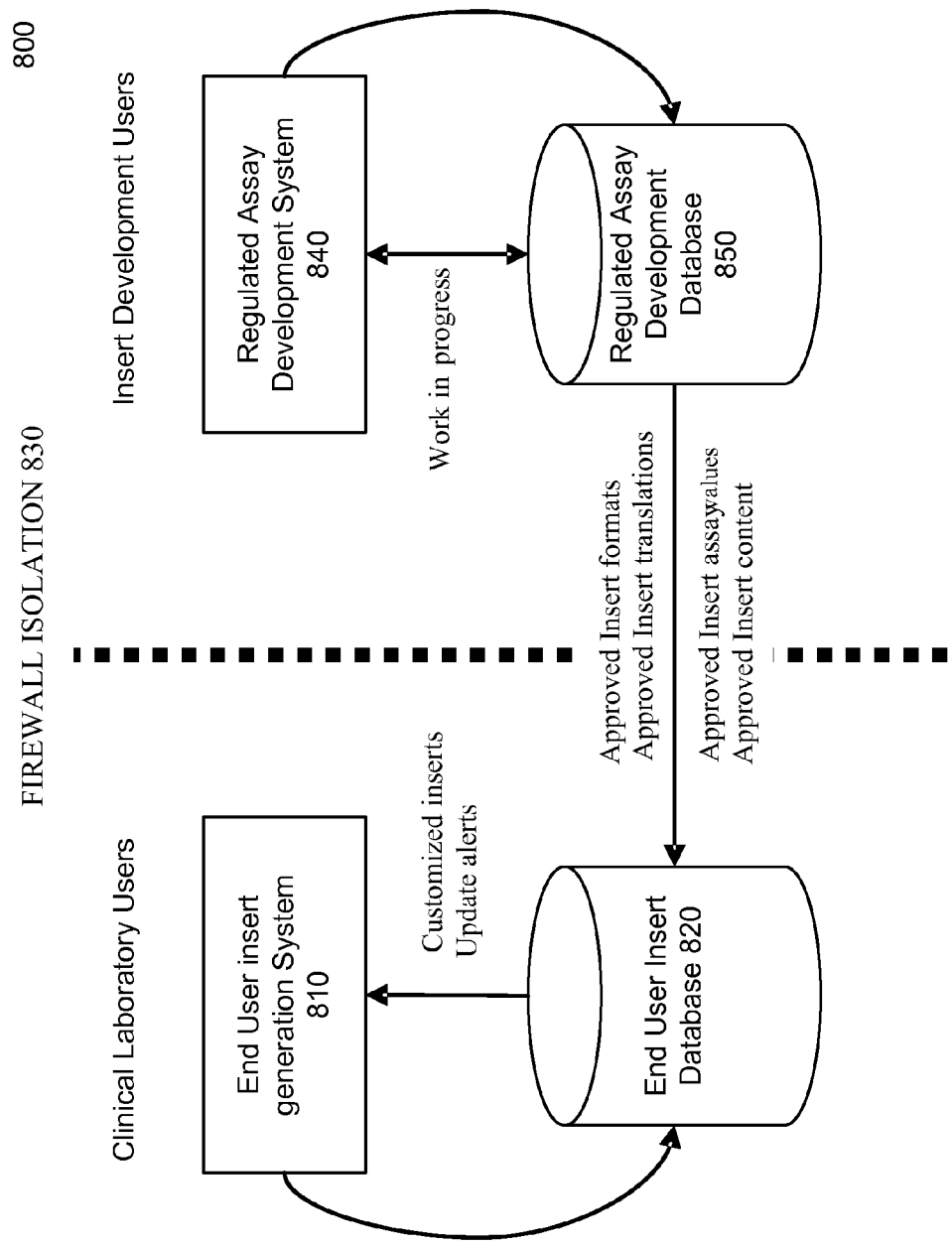
FIG. 8 shows a product insert publication system according to embodiments of the present invention.

FIG. 8 shows a product insert publication system 800 according to embodiments. In one embodiment, two internal systems and one external system can be employed in the generation and delivery of an insert. In other embodiments, only the end user system is used, or just the end user system and the assay development system, thus one or just two of the three systems mentioned below.

A first internal system (not shown) can be a value assignment (VA) web system. In one aspect, the VA system automates the collection of data from researchers using the products, which may be from external researchers or ones from the manufacturer of the control products. In one embodiment, the VA system includes raw data from laboratories that are providing data regarding the resulting parameters. The creator and maintainer of the database can also perform its own studies and upload results. The VA system can be secured and track who accesses and manipulates data. In some embodiments, the data is collected once a first customer identifies that there might be changes to the parameters (e.g. data points outside the range are being seen), or an instrument maker can electronically notify the VA system or the manufacturer via other channels (e.g. phone) when an instrument maker adds a reagent or makes changes. In another embodiment, the customers can continually supply new data and the VA system or another system can analyze the data to see if changes occur (e.g. the system can be tracking the statistical values of the parameters, e.g., on a periodic basis).

A second internal system can be the assay development (AD) database system (also called an insert generator), which includes the regulated AD system 840 that interfaces with a regulated AD database 850. The AD system 840 can take the raw results from the VA system and generate parameters to populate a preliminary insert (which may be just the parameters with some identifying information, such as the corresponding test). This insert can be stored in the AD database 850. The AD database 850 can store inserts that are waiting for approval. If not approved, a new insert can be generated from new data or by a different method, e.g., a different way to determine the high and low. Such a process is labeled "Work in progress" in FIG. 8. The insert can then be analyzed and approved by a person after review. After generation an e-mail can be sent to the reviewers to tell them that their review is required. Once approved, the parameters can be sent to the end user insert database 820. Thus, an update process can replicate the approved contents from the regulated insert development system to the end user insert publication system.

In one embodiment, within the regulated assay development database system 840, there can be a number of information elements used for rendering an insert in the end user insert generation system 810. Each element can include an insert identification number and a version number. When an information element is approved for publication in the regulated assay development system 840, the version number can be incremented (or assigned if this is the initial version) and the element is inserted into the end user insert database 820. In one implementation, there is no communication from the end user insert generation system 810 to the regulated assay development system 840. In one aspect, the next insert that is rendered by the end user insert generation system 810 that includes the updated information element will include the updated element.

The information elements in the end user insert database 820 can include: product description, catalog number, packaging information, CE marks, expiration date, control lot numbers, instructions for use, analyte list, warnings, chart headers, analytes, test methods, units, targets, ranges, references, footnotes, contact information, manufacturing information, and translations for the information elements for each language supported by the system.

A third external system can be the end user system that includes end user insert generation system 810 and the end user insert database 820. Once the insert is approved it can be published to the externally exposed end user insert database 820. Writing to this database can be controlled so that only inserts that have been approved are written. In one aspect, the end user insert database 820 can be isolated from the AD database 850 by a firewall 830. In one embodiment, the end user insert database 820 is not aware of the regulated assay development database 850 and cannot request data from it, but just receives data from a particular port that the development database can write to.

In one aspect, embodiments can start with the existence of a regulated assay development database 850 that has an approval for release process for insert components. The end result of the approval for release process is an update taking place in the end user insert database 820 that reflects the approved change.

Various embodiments can use SQL (Structured Query Language) server for the databases. The web server can be implemented with C#, ASP.net active server pages, or other suitable language. The web server can then communicate with the SQL servers.

Figure 9:
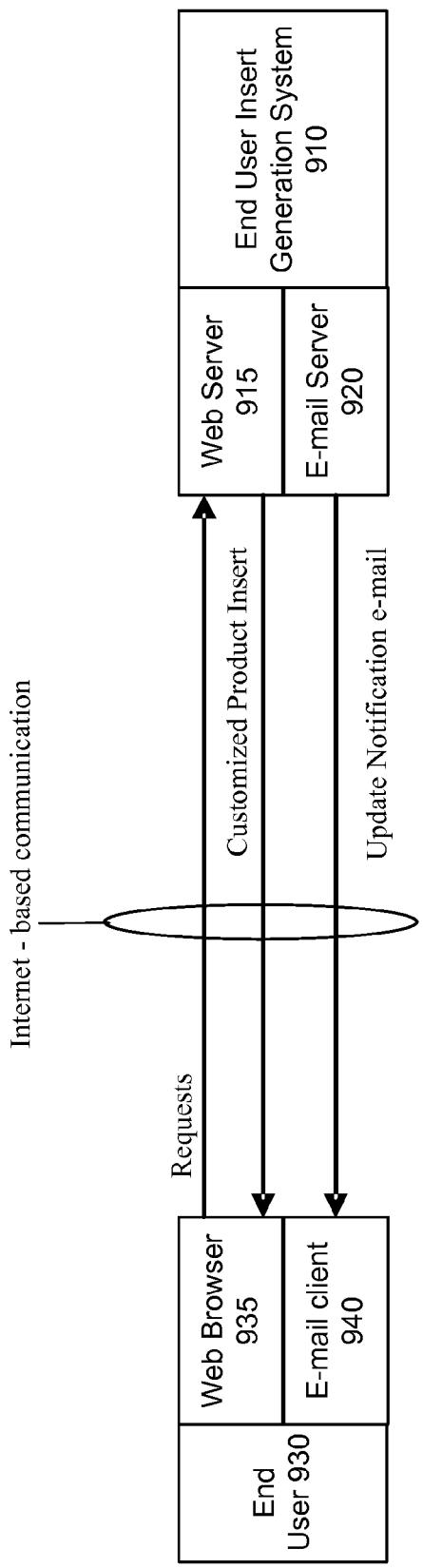
FIG. 9 shows communication between the regulated assay development system and the end user insert generation system according to embodiments of the present invention.

FIG. 9 shows communication between the end user insert generation system and the end user according to embodiments. FIG. 9 shows an end user 930 with a user device that can include a web browser 935 and an e-mail client 940. The end user insert generation system 910 can include a web server 915 and an e-mail server 920. In one embodiment, the end user 930 sends a request for a customized insert, and the web server 915 returns a customized product insert. In one implementation, an update notification can be sent from e-mail server 920 to e-mail client 940. In other implementations, other types of server and client (e.g., for text messages) can be used.

Figure 10:
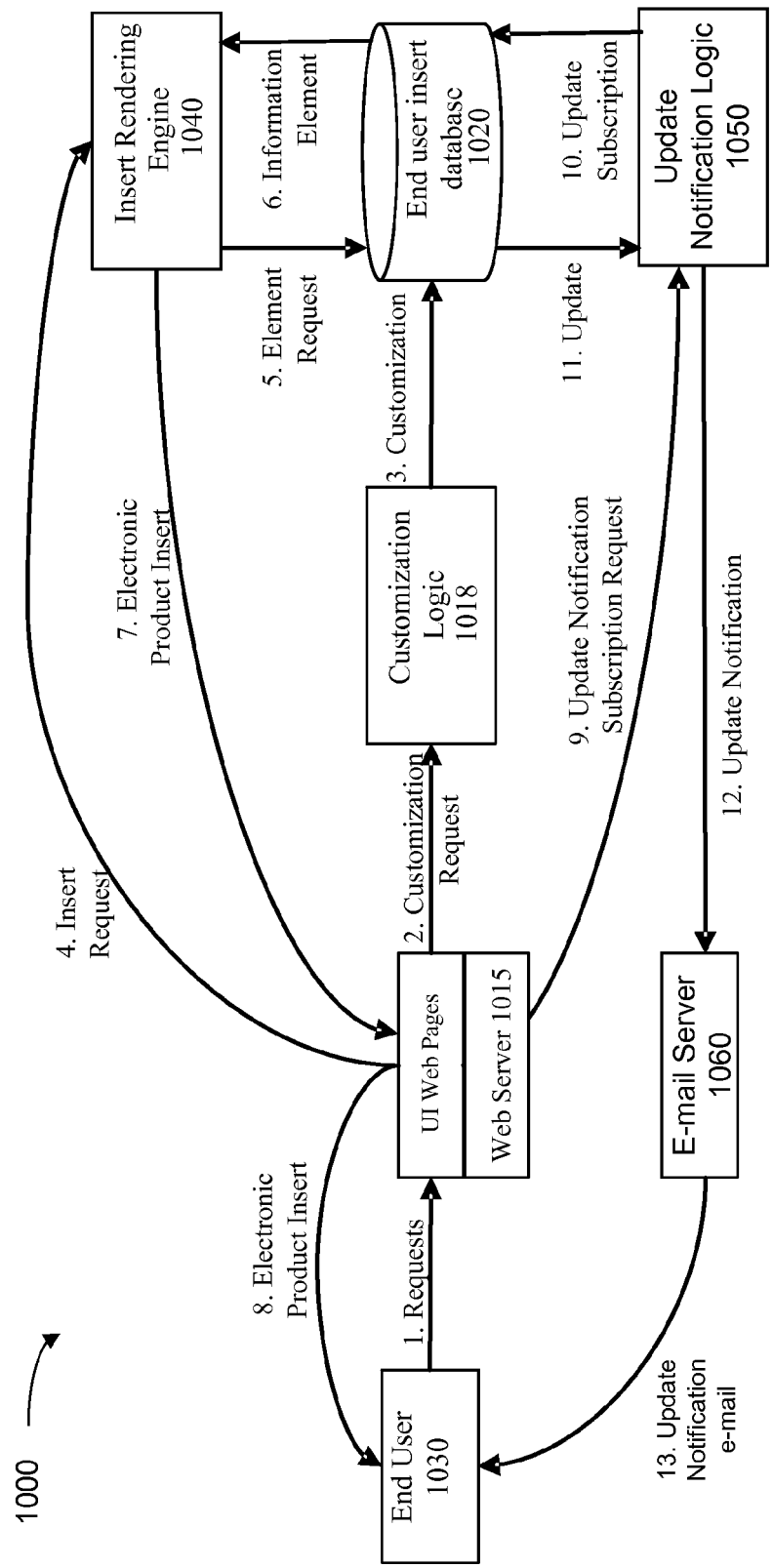
FIG. 10 shows an overview and use of the end user insert generation system according to embodiments of the present invention.

FIG. 10 shows an overview and use of an end user insert generation system 1000 according to embodiments. In one aspect, the steps involved can occur after the parameters have been published into the end user database. In one embodiment, various steps can be performed in different orders than presented. In another embodiment, some steps do have a certain logical progression (e.g. a step depending on one or more previous steps). In yet another embodiment, some steps may be optional.

In step 1, an end user 1030 provides a request for an insert. In various embodiments, the request can provide a product, lot number, language, and any customization. Other examples are described herein.

In step 2, a customization request (e.g. using selections from customer) is sent to customization logic 1018. In one aspect, the customization would be done if the customer does not perform all of the tests for a product. Other examples of customization are provided herein.

In step 3, the customization logic 1018 can organize the customization information to a specific format and send it to the end user insert database 1020. In one embodiment, the end user insert database 1020 can save this customization information with the entry (which can e.g., be a temporary space for a user account), as well as store the parameters for the data charts. In one implementation, the customization information is stored only if the user is logged in; the user may also be required to request to save the customization information. In another embodiment, the customization information is not stored in the database.

In step 4, a request to generate an insert is sent from a web server 1015 (e.g. which can serve the web pages and interact with the end user) to an insert rendering engine 1040. In one embodiment, an entry ID can be sent with the insert request, where the entry ID links the customization information to the insert request. In embodiments where only a guest account is used, the customization information can be sent with the insert request. Alternatively, embodiments can also have a guest entry ID, where the entry is temporarily stored in the end user insert database 1020.

In step 5, the insert rendering engine 1040 requests the desired parameters based on the customization for a particular entry, or just all of the parameters for a product if no customization is done. In one aspect, the entry ID can be used to obtain the proper customization information.

In step 6, the parameters are passed to the rendering engine 1040. As mentioned above, the parameters can be retrieved using various information, such as the test methods, instruments, and user criteria.

In step 7, the generated insert is sent to the web server 1015, e.g., as a PDF. The rendering can use standard templates for formatting. In one embodiment, multiple formats can be provided.

In step 8, the electronic insert is sent to the end user 1030. In one embodiment, the insert is made available for download. In another embodiment, the insert can be sent via e-mail.

In step 9, whether end user 1030 subscribes to a notification is sent to the update notification logic 1050. The update notification logic 1050 can then handle providing updates to the customers that have profiles that have the notification turned on. In one embodiment, only certain entries can be marked for having update notifications provided.

In step 10, a request is sent to find out if an update to the parameters has occurred. In one embodiment, this request can be a scheduled process (e.g. once a night). In another embodiment, an event can be detected which causes the request to be sent. In one implementation, a program running on the update notification logic 1050 or end user insert data base 1020 can detect the event.

In step 11, an update is sent if one was found. In one embodiment, as the data can be date and time stamped, the data that has changed can be found. In another embodiment, a flag is set for an instrument, groups of tests, and/or for individual tests, where a flag is set when one or more parameters for the associated object changes. As examples, insert chart updates can either consist of completely new listings (new instruments or tests), which were not included in the initial release of a product insert, or they could be revised/corrected information for listings that were in the original release of the product insert. All listings can be versioned and time stamped. When the update notification logic module is run, it can look for all listings which have been updated since the last time it ran (based on the time stamps of the listing versions), and then determines what, if any, customers have requested update notifications for those listings.

In step 12, an update notification is sent to the e-mail server 1060. The notification can be tailored specifically to the customer, e.g. include the new data chart or just be a notification. The update notification logic 1050 can also identify which customers need to be notified, and can specify personalizations for the notification to each customer.

In step 13, the update notification is sent to the end user 1030.

Thus, according to some embodiments, an end user insert generation system can be composed of one or more of the following modules: a web server, user interface (UI) web pages, an e-mail server, a customization logic module, an update notification logic module, an insert rendering engine, and the end user insert database.

In some embodiments, the end user communication with the system is with a web browser. In other embodiments, the communication can occur through a text messaging interface, FTP interface, or other interface that can occur over a network.

In one embodiment, web communication from users is handled by UI web pages executing on the web server. The web server receives requests from the end user's web browser. The requests are evaluated by the UI web pages residing on the web server and dispatched to the appropriate logic module. When an electronic product insert is prepared with the requested customizations by the insert rendering engine, it is delivered by the web server to the end user.

In various embodiments, the UI web pages can handle the following operations: selection of website language, selection of product, selection of lot number, selection of insert language, selection of chart units, selection of instructions for use, selection of specific instruments, selection of specific methods, viewing the product insert, saving the insert customization, printing the product insert, creating a user profile, updating a user profile, and subscribing to update notifications. On receiving the requested operation, the appropriate logic module can be dispatched.

In some embodiments, the update notification logic 1050 can handle requests for update notifications. In one embodiment, it enters an update subscription for an end user in the end user insert database 1020 with the associated information elements associated with the end user. Periodically, the update notification logic 1050 can scan the end user insert database 1020 and identify information elements whose version has changed since the last check. These elements (parameters) can be the updates for which notifications may need to be sent to the user. The update notification logic 1050 can check the update subscription list for any of the identified information elements. For those update subscriptions that have updated information elements, an update notification e-mail can be prepared and dispatched to the e-mail server 1015, which sends it to the end user who requested the update notification subscription.

The customization logic 1050 can record customizations associated with an end user in the end user insert database 1020. The customizations can be used to select the set of information elements used by the insert rendering engine to produce the customized product insert.

The insert rendering engine 1040 can contain the logic to produce an electronic insert in the portable document format (PDF) from a selected set of information elements. The set of information elements (parameters) used to produce the insert depends on the customizations specific for the user the insert is being produced for.

Figure 11:
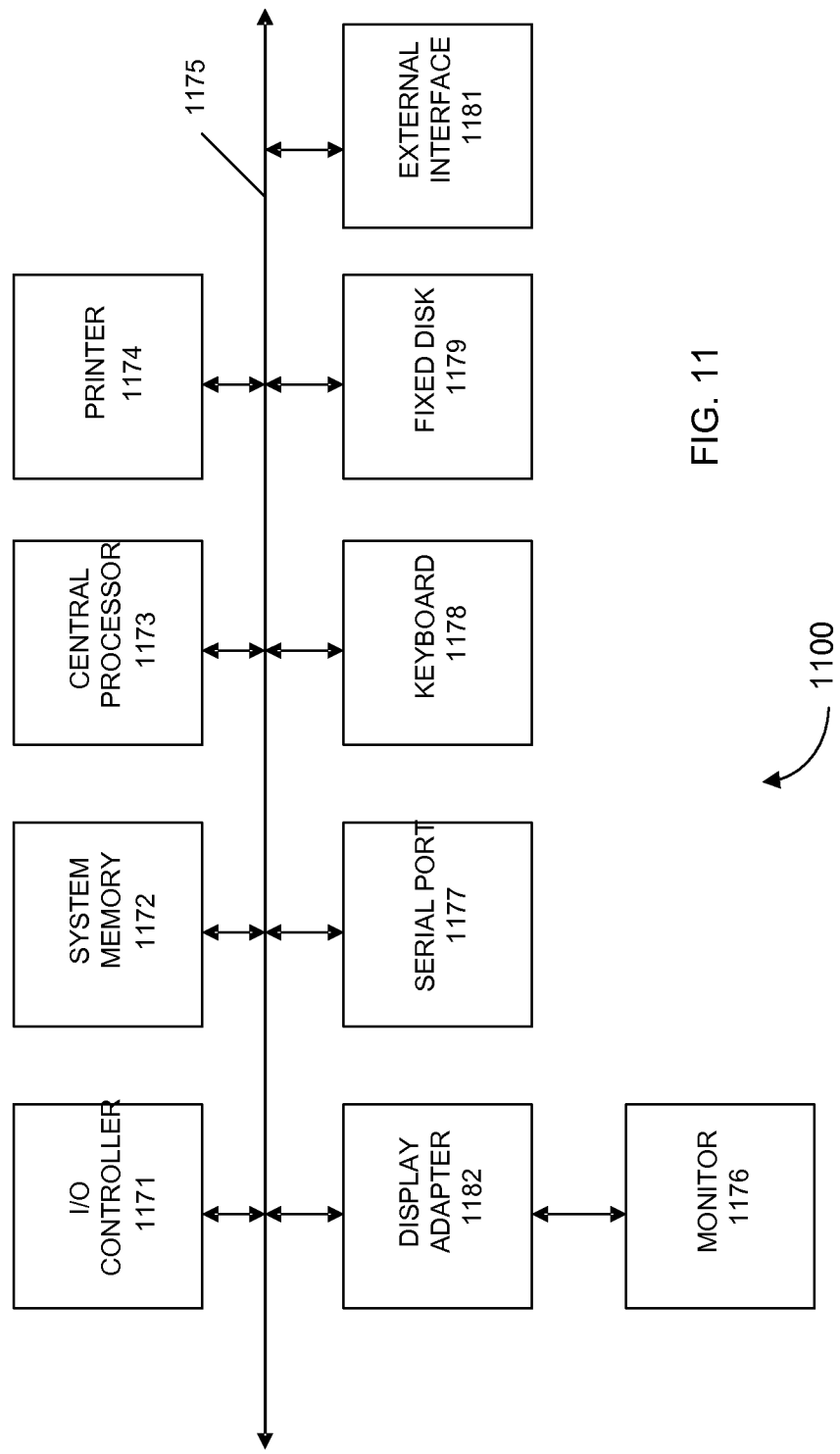
FIG. 11 shows a block diagram of an exemplary computer system usable with system and methods according to embodiments of the present invention.

Any of the computer systems mentioned herein may utilize any suitable number of subsystems. Examples of such subsystems are shown in FIG. 11 in computer system 1100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 11 are interconnected via a system bus 1175. Additional subsystems such as a printer 1174, keyboard 1178, fixed disk 1179, monitor 1176, which is coupled to display adapter 1182, and others are shown. Peripherals and input/output (I/O) devices, which couple to I/O controller 1171, can be connected to the computer system by any number of means known in the art, such as serial port 1177. For example, serial port 1177 or external interface 1181 can be used to connect computer system 1100 to a wide area network such as the Internet, a mouse input device, or a scanner. The interconnection via system bus 1175 allows the central processor 1173 to communicate with each subsystem and to control the execution of instructions from system memory 1172 or the fixed disk 1179, as well as the exchange of information between subsystems. The system memory 1172 and/or the fixed disk 1179 may embody a computer readable medium.

A computer system can include a plurality of the same components or subsystems, e.g., connected together by external interface 1181. In some embodiments, computer systems, subsystem, or apparatuses can communicate over a network. In such instances, one computer can be considered a client and another computer a server. A client and a server can each include multiple systems, subsystems, or components, mentioned herein.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of distributing updated parameters of operating results for one or more control products used in biological reactions, the method comprising:
   receiving, from a user by a server system, a request to customize delivery of one or more update notifications for one or more control products, wherein the one or more update notifications are to be sent when one or more parameters associated with the one or more control products have been updated since sending a previous update notification to the user;
   accessing, by the server system, a database to determine whether the one or more parameters have been updated since the previous update notification, each test operable to test one or more analytes in a biological reaction to generate one or more analyte results and operable to test the one or more control products in the biological reaction to generate one or more control results, the one or more control results operable to confirm a quality of the one or more analyte results, wherein the request identifies the one or more analytes and the one or more control products;
   when the one or more parameters have been updated since the previous update notification, receiving, by the server system from the database, data that has been updated since the previous update notification, wherein the data comprises one or more of the following: a date or time stamp of the updated parameters, a flag identifying a change from the previous update notification, and the one or more parameters; and
   sending by the server system, the update notification to the user, wherein the update notification includes at least part of the data that has been updated since receiving a previous request.

2. The method of claim 1, wherein accessing the database identifies the one or more parameters corresponding to the request, wherein the one or more parameters specify one or more updated acceptable values for the one or more control results for confirming the quality of the one or more analyte results.

3. The method of claim 1, further comprising:
   receiving by the server system, customization information from the user, wherein the identified parameters are based on the customization information.

4. The method of claim 1, wherein the request is received through a user interface on a web page, and wherein the user interface is operable to allow the user to select a website language, product, lot number, language used in providing information with an insert, chart units, and instructions for use as customization information.

5. The method of claim 1, where the data that has been updated since receiving the previous request are sent as a data chart.

6. The method of claim 1, wherein the update notification is an automated notification request that is sent independent of a request to send updates from the user.

7. The method of claim 1, further comprising:
   receiving customization information from one or more customization request from a plurality of users, wherein the identified parameters are based on the customization information; and
   storing the customization information, wherein sending the update notification to the user includes using the stored customization information to determine which users have requested parameters that have changed.

8. The method of claim 1, wherein the one or more parameters specify one or more updated acceptable values for the one or more control results for confirming the quality of the one or more analyte results.

9. The method of claim 8, wherein the one or more updated acceptable values for the one or more control results is one or more ranges of acceptable values.

10. The method of claim 8, wherein the one or more updated acceptable values for the one or more control results is one or more target values.

11. The method of claim 1, wherein the request identifies a type of instrument operable to test the one or more control products to generate the one or more control results.

12. The method of claim 1, wherein the request identifies a reagent operable to use with the one or more control products.

13. A method of customizing parameters of operating results for one or more control products used in biological reactions, the method comprising:
   receiving, by a server system, a customization request from a user, wherein the customization request identifies one or more selections of customization information, the selections corresponding to the customization information to be provided to the user;
   sending the selected customization information to a database, wherein the database comprises first information about the biological reactions to generate one or more analyte results, and second information of the one or more control products in the biological reactions to generate one or more control results operable to confirm a quality of the one or more analyte results;
   sending, by the server system to a rendering engine, a request to generate an insert, wherein the insert provides information about a product, the request including an entry ID, wherein the entry ID links the selected customization information with the request;
   using, by the rendering engine, the entry ID to access the database to request the selected customization information and one or more parameters corresponding to the selected customization information;

rendering, by the rendering engine, the insert by using the selected customization information and the one or more parameters; and sending the insert to the user.

14. The method of claim 13, wherein the customization information is received from a plurality of users, wherein the identified parameters are based on the customization information.

15. The method of claim 13, wherein the customization request includes a product, lot number, or language associated with the one or more parameters.

16. The method of claim 13, further comprising:
providing a user interface for the user to submit the customization request.

17. The method of claim 13, further comprising:
providing a user interface for the user to create a plurality of profiles.

18. The method of claim 17, further comprising:
creating the plurality of profiles for the user, each profile containing different information.

19. The method of claim 18, wherein the different information includes one or more selected from a group consisting of product name, lot number, tests to be performed, and instrument being used to perform a test.

20. The method of claim 13, further comprising:
organizing, by the server system, the customization information to a specific format.

21. A computer program product comprising a non-transitory tangible computer readable medium storing a plurality of instructions for controlling a processor to perform an operation for distributing updated parameters of operating results for one or more control products used in biological reactions, the operation comprising:

receiving, from a user, a request to customize delivery of one or more update notifications for one or more control products, wherein the one or more update notifications are to be sent when one or more parameters associated with the one or more control products have been updated since sending a previous update notification to the user;

accessing a database to determine whether the one or more parameters have been updated since the previous update notification, each test operable to test one or more analytes in a biological reaction to generate one or more analyte results and operable to test the one or more control products in the biological reaction to generate one or more control results, the one or more control results operable to confirm a quality of the one or more analyte results, wherein the request identifies the one or more analytes and the one or more control products;

when the one or more parameters have been updated since the previous update notification, receiving, from the database, data that has been updated since the previous update notification, wherein the data comprises one or more of the following: a date or time stamp of the updated parameters, a flag identifying a change from the previous update notification, and the one or more parameters; and sending the update notification to the user, wherein the update notification includes at least part of the data that has been updated since receiving a previous request.

22. A computer program product comprising a non-transitory tangible computer readable medium storing a plurality of instructions for controlling a processor to perform an operation for customizing parameters of operating results for one or more control products used in biological reactions, the operation comprising:

receiving a customization request from a user, wherein the customization request identifies one or more selections of customization information, the selections corresponding to the customization information to be provided to the user;

sending the selected customization information to a database, wherein the database comprises first information about the biological reactions to generate one or more analyte results, and second information of the one or more control products in the biological reactions to generate one or more control results operable to confirm a quality of the one or more analyte results;

sending, to a rendering engine, a request to generate an insert, wherein the insert provides information about a product, the request including an entry ID, wherein the entry ID links the selected customization information with the request;

using, by the rendering engine, the entry ID to access the database to request the selected customization information and one or more parameters corresponding to the selected customization information;

rendering, by the rendering engine, the insert by using the selected customization information and the one or more parameters; and sending the insert to the user.

23. The computer program product of claim 21, wherein accessing the database identifies the one or more parameters corresponding to the request, wherein the one or more parameters specify one or more updated acceptable values for the one or more control results for confirming the quality of the one or more analyte results.

24. The computer program product of claim 21, wherein the operation further comprises:
receiving by the server system, customization information from the user, wherein the identified parameters are based on the customization information.

25. The computer program product of claim 21, wherein the request is received through a user interface on a web page, and wherein the user interface is operable to allow the user to select a website language, product, lot number, language used in providing information with an insert, chart units, and instructions for use as customization information.

26. The computer program product of claim 21, where the data that has been updated since receiving the previous request are sent as a data chart.

27. The computer program product of claim 21, wherein the update notification is an automated notification request that is sent independent of a request to send updates from the user.

28. The computer program product of claim 21, wherein the operation further comprises:
receiving customization information from one or more customization request from a plurality of users, wherein the identified parameters are based on the customization information; and storing the customization information, wherein sending the update notification to the user includes using the stored customization information to determine which users have requested parameters that have changed.

29. The computer program product of claim 21, wherein the one or more parameters specify one or more updated acceptable values for the one or more control results for confirming the quality of the one or more analyte results.

30. The computer program product of claim 29, wherein the one or more updated acceptable values for the one or more control results is one or more ranges of acceptable values.

31. The computer program product of claim 29, wherein the one or more updated acceptable values for the one or more control results is one or more target values.

32. The computer program product of claim 21, wherein the request identifies a type of instrument operable to test the one or more control products to generate the one or more control results.

33. The computer program product of claim 21, wherein the request identifies a reagent operable to use with the one or more control products.

34. The computer program product of claim 22, wherein the customization information is received from a plurality of users, wherein the identified parameters are based on the customization information.

35. The computer program product of claim 22, wherein the customization request includes a product, lot number, or language associated with the one or more parameters.

36. The computer program product of claim 22, wherein the operation further comprises:
providing a user interface for the user to submit the customization request.

37. The computer program product of claim 22, wherein the operation further comprises:
providing a user interface for the user to create a plurality of profiles.

38. The computer program product of claim 37, wherein the operation further comprises:
creating the plurality of profiles for the user, each profile containing different information.

39. The computer program product of claim 38, wherein the different information includes one or more selected from a group consisting of product name, lot number, tests to be performed, and instrument being used to perform a test.

40. The computer program product of claim 22, wherein the operation further comprises:
organizing, by the server system, the customization information to a specific format.

* * * * *